US009918960B2

(12) United States Patent
Arnon et al.

(10) Patent No.: US 9,918,960 B2
(45) Date of Patent: Mar. 20, 2018

(54) TOPICAL OILY FOAM COMPOSITIONS

(71) Applicant: PERRIGO ISRAEL PHARMACEUTICALS LTD., Bnei Brak (IL)

(72) Inventors: Michal N. Arnon, Midreshet Ben-Gurion (IL); Tatiana Kamenetsky, Beer Sheva (IL)

(73) Assignee: PERRIGO ISRAEL PHARMACEUTICALS LTD., Bnei Brak (IL)

( * ) Notice: Subject to any disclaimer, the term of this patent is extended or adjusted under 35 U.S.C. 154(b) by 0 days.

(21) Appl. No.: 15/643,888

(22) Filed: Jul. 7, 2017

(65) Prior Publication Data

US 2017/0304257 A1    Oct. 26, 2017

Related U.S. Application Data

(62) Division of application No. 14/233,198, filed as application No. PCT/IL2012/000281 on Jul. 19, 2012, now Pat. No. 9,724,324.

(60) Provisional application No. 61/509,888, filed on Jul. 20, 2011.

(51) Int. Cl.
*A61K 9/12* (2006.01)
*A61K 31/351* (2006.01)
*A61K 31/59* (2006.01)
*A61K 9/00* (2006.01)
*A61K 47/14* (2017.01)
*A61K 47/44* (2017.01)

(52) U.S. Cl.
CPC .......... *A61K 31/351* (2013.01); *A61K 9/0014* (2013.01); *A61K 9/122* (2013.01); *A61K 31/59* (2013.01); *A61K 47/14* (2013.01); *A61K 47/44* (2013.01)

(58) Field of Classification Search
CPC .......... A61Q 7/02; A61Q 19/04; A61Q 19/02; A61Q 19/004; A61Q 7/00
See application file for complete search history.

(56) References Cited

U.S. PATENT DOCUMENTS

| | | | |
|---|---|---|---|
| 6,126,920 | A | 10/2000 | Jones et al. |
| 6,730,288 | B1 | 5/2004 | Abram |
| 7,029,659 | B2 | 4/2006 | Abram |
| 8,343,945 | B2 | 1/2013 | Tamarkin |
| 2009/0130029 | A1 | 5/2009 | Tamarkin et al. |
| 2009/0227568 | A1 | 9/2009 | Gizurarson |
| 2010/0310476 | A1 | 12/2010 | Tamarkin et al. |

FOREIGN PATENT DOCUMENTS

| | | |
|---|---|---|
| WO | 2009/098595 | 8/2009 |
| WO | 2010/125470 | 11/2010 |

OTHER PUBLICATIONS

International Search Report, International Application No. PCT/IL 2012/000281 (dated Dec. 24, 2012).
EP, European Search Report, European Application No. 12815080.2 (dated Nov. 24, 2014).
International Preliminary Report on Patentability, International Application No. PCT/IL2012/000281 (dated Jan. 30, 2014).
Mudge, S.M., Fatty Alcohols—a review of their natural synthesis and environmental distribution, The Soap and Detergent Association, 2005, retrieved from the internet on Nov. 12, 2012, http://www.aciscience.org/docs/Fatty_Alcohols_Mudge_2005.pdf.
Buy Permethrin Online, web page of Northwest Pharmacy, 2007, retrieved from the internet on Nov. 12, 2012, http://www.northwestpharmacy.com/Products/71841/buy-Permethrin--online.aspx.

*Primary Examiner* — Nannette Holloman
(74) *Attorney, Agent, or Firm* — Thompson Hine LLP

(57) ABSTRACT

Topical alcohol-free thermo labile oily foam composition comprising
(i) at least one active pharmaceutical ingredient or ectoparasitic active ingredient;
(ii) at least about 20% w/w of at least one lipophilic component;
(iii) at least about 10% w/w of at least one non-ionic surfactant;
(iv) at least about 0.5% w/w of at least one fatty alcohol or fatty acid or ester thereof with melting point above 30° C., and;
(v) at least about 7% w/w of propellant selected from propane, butane, isobutane and combinations thereof;
said composition optionally comprising at least about 5% to about 70% w/w of a hydrophilic component, optionally comprising up to about 5% w/w hydrogenated oil and optionally comprising a penetration enhancer.

14 Claims, No Drawings

TOPICAL OILY FOAM COMPOSITIONS

FIELD OF THE INVENTION

The present invention provides topical alcohol-free thermo labile oily foam composition for dermal or transdermal delivery of at least one active pharmaceutical ingredient or ectoparasitic active ingredient. The compositions of the present invention are particularly useful for lipophilic and hydrous sensitive pharmaceutical or ectoparasitic active ingredients.

BACKGROUND OF THE INVENTION

Various foams for topical delivery of active pharmaceutical ingredients are known in the art. However, the application of these foam compositions, either stable foams or quick breaking foams, requires rubbing or application of shear force to collapse the foam structure and to spread the collapsed composition on the application site.

U.S. Pat. No. 6,126,920 discloses foam compositions containing water or alcohols which have a disadvantage of increased irritation. In addition, although the specifications of the mentioned patent disclose quick breaking foam compositions that minimize rubbing of the target site, the need for rubbing is not completely eliminated.

U.S. Pat. No. 6,730,288 and U.S. Pat. No. 7,029,659 are directed to pharmaceutical foam compositions comprising an aqueous solvent, making them unsuitable for lipophilic or hydrous sensitive therapeutically active agents.

There is a need to develop a foamable composition which is lipophilic and completely anhydrous that collapses at the application site without requiring rubbing or application of shear force.

SUMMARY OF INVENTION

The present invention provides topical alcohol-free thermo labile oily foam compositions for dermal and/or transdermal delivery of at least one active pharmaceutical ingredient or ectoparasitic active ingredient.

In one aspect the topical alcohol-free thermo labile oily foam compositions of the present invention comprise (i) a therapeutically effective amount of at least one active pharmaceutical ingredient; (ii) an organic solvent system comprising at least one lipophilic component and optionally at least one hydrophilic component; (iii) at least about 10% w/w of at least one non-ionic surfactant; (iv) about 0.5% to about 30% w/w of at least one fatty alcohol or fatty acid or esters thereof with melting point above about 30° C.; (v) propellant in an amount of about 7% to 20% w/w.

In another aspect the topical alcohol-free thermo labile oily foam compositions of the present invention comprise (i) an effective amount of at least one ectoparasitic active ingredient; (ii) an organic solvent system comprising at least one lipophilic component and optionally at least one hydrophilic component; (iii) at least about 10% w/w of at least one non-ionic surfactant; (iv) about 0.5% to about 30% w/w of at least one fatty alcohol or fatty acid or esters thereof with melting point above about 30° C.; (v) propellant in an amount of about 7% to 20% w/w.

Further provided by the present invention is an oily foam carrier system for a pharmaceutical preparation wherein said carrier system comprises (a) an organic solvent system comprising at least one lipophilic component and optionally at least one hydrophilic component; (b) at least about 10% w/w of at least one non-ionic surfactant; (c) about 0.5% to about 30% w/w of at least one fatty alcohol or fatty acid or esters thereof with melting point above about 30° C.; (d) propellant in an amount of about 7% to 20% w/w.

In one aspect, the present invention provides a method of using the topical alcohol-free thermo labile oily foam compositions of the present invention comprising topically applying said oily foam compositions to the treatment area.

In another aspect, the present invention provides a method of treating, alleviating or preventing: (i) a dermatological or mucosal disease and/or disorder and, (ii) ectoparasitosis, comprising topically administering to a subject in need thereof an effective amount of the topical alcohol-free thermo labile oily foam compositions of the present invention.

An embodiment of the present invention is a method of manufacture of the said topical alcohol-free thermo labile oily foam composition comprising combining the above-described components, excluding the propellant, heating the mixture, homogenizing it, optionally cooling the mixture, pouring the resulting mixture into an aluminum aerosol spraying canister, attaching a valve to the canister, supplying vacuum to the canister and sealing the canister. A hydrocarbon propellant mixture is then added and an actuator is assembled on the valve.

Another embodiment of the present invention is providing said topical alcohol-free thermo labile oily foam compositions in a pressurized aerosol spraying canister, preferably aluminum.

An additional aspect of the present invention is a process of preparation of said topical alcohol-free thermo labile oily foam compositions comprising providing the active pharmaceutical ingredient or ectoparasitic active ingredient in a first vessel, mixing the carrier system components in a second vessel to obtain a carrier mixture, heating and then cooling the obtained carrier mixture, adding the contents of the first vessel to the cooled carrier mixture to obtain an oily composition, optionally homogenizing the composition, pouring the obtained composition into an pressurized aerosol spraying canister, attaching a valve to the canister, applying vacuum to the canister and sealing the canister, followed by adding a hydrocarbon propellant mixture, and attaching an actuator onto canister valve.

As an alternative to pouring the obtained oily composition into said canister, the composition may be further cooled and stored.

DETAILED DESCRIPTION

The topical alcohol-free thermo labile oily foam compositions described in the present invention are suitable for topical, dermal or transdermal delivery, of at least one therapeutically active agent or ectoparasitic active ingredient, and are especially advantageous for dermal or transdermal delivery of at least one lipophilic or hydrous sensitive active pharmaceutical ingredients or ectoparasitic active ingredient. Said compositions can be administered by direct application to the skin.

The term "thermo labile" is intended to mean that the compositions of the present invention are easily affected, i.e. the foam structure collapses, by moderate heating, such as approximately skin temperature, preferably between about 30° C. to about 40° C.

The term "readily collapsing" or "readily collapsible" is intended to mean that the foam structure of topical alcohol-free thermo labile oily foam composition of the present invention collapses after its application to the treatment area without rubbing or application of sheer force.

The term "skin" is intended to mean skin, scalp, mucosal areas, and body cavities which can be hairless or covered with hair and may have wrinkles.

The term "substantially anhydrous" is intended to mean less than about 3 wt % water.

The term "Alcohol free" is intended to mean free of $C_1$ to $C_3$ alkanols.

The term "ectoparasitic active ingredient" refers to the composition component that provides a pesticidal or insecticidal effect on the body of man or animals in need thereof.

The term "hydrous sensitive therapeutically active pharmaceutical ingredient" and "hydrous sensitive ectoparasitic active ingredient" is intended to mean a therapeutically active pharmaceutical ingredient or ectoparasitic active ingredient which is generally considered by persons skilled in the art as not stable in aqueous environment for a long period of time, due to degradation, changes in its crystalline form, aggregation or coagulation of its suspended particles, or any other chemical or physical change to its desired original chemical or physical properties, as required by the composition of the present invention.

The term "insoluble" is intended to mean a therapeutically active ingredient or ectoparasitic active ingredient which dissolves in water to give an aqueous solution with a concentration of less than 0.001M at room temperature.

The term "slightly soluble" is intended to mean a therapeutically active ingredient which dissolves in water to give an aqueous solution with a concentration of at least 0.001M at room temperature and less than 0.1 moles per liter at room temperature.

The term "lipophilic therapeutically active ingredient" and "lipophilic ectoparasitic active ingredient" is intended to mean therapeutically active ingredient or ectoparasitic active ingredient which is insoluble or is only slightly soluble in water.

The term "% w/w" is intended to mean weight by weight percent based on the topical alcohol-free thermo labile oily foam composition excluding the propellant unless otherwise specified. All amounts depicted in "%" are weight by weight unless specifically indicated otherwise.

The term "carrier system" is intended to mean a combination of all composition components excluding the active pharmaceutical ingredient or ectoparasitic active ingredient and the propellant.

The term "ectoparasite" is intended to mean an organism that lives on a host organism, from which it obtains nutriment, without contributing to the survival of its host (e.g. ticks, lice, fleas and mites).

The term "ectoparasitosis" is intended to mean an ectoparasitic infestation or infection of the skin, scalp or genitals, such as scabies and/or pediculosis.

The terms "therapeutically active agent", "therapeutically active ingredient" and "active pharmaceutical ingredient" are used interchangeably.

In one aspect the topical alcohol-free thermo labile oily foam compositions of the present invention comprise (i) a therapeutically effective amount of at least one active pharmaceutical ingredient; (ii) at least about 20% w/w and more particularly about 40% to about 95% w/w of an organic solvent system comprising at least one lipophilic component and optionally at least one hydrophilic component; (iii) at least about 10% w/w and more particularly about 10% to about 70% w/w of at least one non-ionic surfactant; (iv) at least about 0.5% to about 30% w/w of at least one fatty alcohol, fatty acid or esters thereof with melting point above about 30° C. (such as but not limited to cetyl alcohol and stearyl alcohol); (v) propellant in an amount of about 7% to about 20% w/w based on the total weight of the composition components excluding the propellant.

In a further aspect the topical alcohol-free thermo labile oily foam compositions of the present invention can comprise (i) an effective amount of at least one ectoparasitic active ingredient; (ii) at least about 20% w/w and more particularly about 40% to about 95% w/w of an organic solvent system comprising at least one lipophilic component and optionally at least one hydrophilic component; (iii) at least about 10% w/w and more particularly about 10% to about 70% w/w of at least one non-ionic surfactant; (iv) at least about 0.5% to about 30% w/w of at least one fatty alcohol, fatty acid or esters thereof with melting point above about 30° C. (such as but not limited to cetyl alcohol and stearyl alcohol); (v) propellant in an amount of about 7% to about 20% w/w based on the total weight of the composition components excluding the propellant.

The present invention discloses a topical alcohol-free thermo labile oily foam carrier system, comprising (i) an organic solvent system comprising at least one lipophilic component and optionally at least one hydrophilic component; (ii) at least about 10% w/w and more particularly about 10% to about 70% w/w of at least one non-ionic surfactant; (iii) about 0.5% to about 30% w/w of at least one fatty alcohol, fatty acid or esters thereof with melting point above about 30° C. (such as but not limited to cetyl alcohol and stearyl alcohol); (iv) propellant in an amount of about 7% to about 20% w/w. Said carrier system is intended to be formulated together with an active pharmaceutical ingredient or ectoparasitic active ingredient to create a system for delivering an effective amount of an active pharmaceutical ingredient or ectoparasitic active ingredient to the site of application on a subject in the need thereof.

The amount of the active pharmaceutical ingredient or ectoparasitic active ingredient is included in the calculation of the topical alcohol-free thermo labile oily foam compositions; however it is excluded from the calculation of the carrier system components.

The topical alcohol-free thermo labile oily foam compositions of the present invention are suitable for topical administration to mammalian skin, preferably human skin.

The topical alcohol-free thermo labile oily foam compositions of the present invention can be used for topically treating, alleviating or preventing conditions and/or diseases of the skin. Non limiting examples of said conditions and diseases are inflammation, psoriasis, hyperkeratotic dermatosis, pruritic manifestations of corticosteroid-responsive dermatoses, eczema, skin infection, impetigo, burns, cuts, and atopic dermatitis.

The topical alcohol-free thermo labile oily foam compositions of the present invention can be further used for topically treating, alleviating or preventing ectoparasitosis, non-limiting examples of ectoparasitosis causing parasites include ticks, lice, fleas and mites. Preferably, the topical alcohol-free thermo labile oily foam compositions of the present invention can be used for topically treating, alleviating or preventing scabies and/or pediculosis.

The topical alcohol-free thermo labile oily foam compositions of the present invention comprise at least about 10% w/w of at least one non-ionic surfactant. Non-limiting examples of non-ionic surfactants comprise Cetomacrogol 1000, Decyl glucoside, Glyceryl laurate, Isoceteth-20, Lauryl glucoside, Nonoxynol-9, Nonoxynols, Poloxamer, Poloxamer 407, Polysorbate, Polysorbate 20, Polysorbate 80, Sorbitan monostearate, Sorbitan tristearate Triton X-100, and Methyl glucose sesquistearate.

The topical alcohol-free thermo labile oily foam compositions of the present invention comprise between about 0.5% to about 30% of at least one fatty alcohol, fatty acid or esters thereof with melting point above about 30° C.

In a preferred embodiment of the present invention said compositions comprise from about 3% w/w to about 20% w/w of cetyl alcohol, from about 0.5% w/w to about 10% w/w stearyl alcohol.

The topical alcohol-free thermo labile oily foam compositions of the present invention comprise propellant in an amount of about 7% to 20% w/w. It should be noted, that the composition of the present invention can total more than 100% w/w after the propellant has been added. Suitable gas propellants comprise propane, butane, isobutane, dichloro difluoro methane, dichloro tetrafluoro ethane, octafluoro cyclobutane, and mixtures thereof.

The topical alcohol-free thermo labile oily foam compositions of the present invention comprise an organic solvent system comprising at least one lipophilic component and optionally at least one hydrophilic component.

The lipophilic component is preferably oil, selected from, but not limited to, vegetable oils, hydrocarbons such as, but not limited to, mineral oil and petrolatum, glycerides selected from but not limited to mono di and tri esters of fatty acids and polyols, esters of polyalkylene glycols, ethers of polyalkylene glycols, fatty alcohols, and combinations thereof. More preferably, the lipophilic component is selected from castor oil, oleyl alcohol, caprylic/capric triglyceride, and combinations thereof. The amount of lipophilic component may be present in an amount of at least about 20% and more particularly about 40% to about 95% w/w.

The hydrophilic component is preferably selected from polyols dimethyl isosorbide, polyethylene glycols and combinations thereof. More preferably, the hydrophilic component is selected from Hexylene Glycol, MPEG 350, dimethyl isosorbide, and combinations thereof. The amount of hydrophilic component is from about 5% to about 70% w/w and more particularly at least about 15% w/w.

The topical alcohol-free thermo labile oily foam compositions of the present invention may further comprise hydrogenated oil wherein the melting point of the hydrogenated oil is from a temperature of about 70° C. to about 110° C. The hydrogenated oil concentration can be present in an amount of from about 0.5% to about 5% w/w. Compositions containing hydrogenated oil provide a more viscous composition once the foam structure collapses on the treatment area. Preferably, the hydrogenated oil is hydrogenated castor oil, tri-hydroxy stearyl and combinations thereof.

The hydrogenated oil is suspended in the formulation. Due to the hydrogenated castor oil, the topical alcohol-free thermo labile oily foam compositions of the present invention remain at the application site without dribbling, hence without spotting, staining, wetting or causing any discomfort, that an application of a more viscous composition might cause. As such, said compositions provide a beneficial method of application to the skin or to body cavities such as the vagina, the rectum, the nasal cavities, the mouth, the eyes, the ear canal and the like, where it is desirable that the applied composition will remain in place without spilling. In a further aspect, the lingering of said compositions at the application site allows good retention and thus contributes to the availability of the active pharmaceutical ingredient or ectoparasitic active ingredient and confers an improved therapeutic effect.

The topical alcohol-free thermo labile oily foam compositions of the present invention do not dry after application to the treatment site and until the required washing is carried out, allowing for example to bandages to the treated area without it adhering to the skin which in turn allows easy removal.

The present invention provides substantially anhydrous topical alcohol-free thermo labile oily foam compositions. Preferably, said compositions contain no water, however, it should be noted that while water is not added as a separate ingredient, the topical alcohol-free thermo labile oily foam compositions of the present invention may comprise trace amounts of water originating from one or more of the other ingredients or absorbed from the environment.

The topical alcohol-free thermo labile oily foam compositions of the present invention are preferably free of $C_1$ to $C_3$ alkanols, however, it should be noted that while $C_1$ to $C_3$ alkanols are not added as a separate ingredient, the topical alcohol-free thermo labile oily foam compositions of the present invention may comprise trace amounts of $C_1$ to $C_3$ alkanols originating from one or more of the other ingredients.

In one embodiment, the topical alcohol-free thermo labile oily foam compositions of the present invention comprise at least one active pharmaceutical ingredient or ectoparasitic active ingredient in a solubilized or suspended state, if more than one active pharmaceutical ingredient or ectoparasitic active ingredient is comprised, said ingredients can be solubilized, suspended or be present in the composition in a combination thereof.

The topical alcohol-free thermo labile oily foam compositions of the present invention comprise an effective amount of at least one therapeutically active ingredient or ectoparasitic active ingredient. Said compositions are advantageous for therapeutically active ingredients or ectoparasitic active ingredient that are lipophilic or hydrous sensitive. Non-limiting examples of said lipophilic or hydrous active pharmaceutical ingredients or ectoparasitic active ingredients are anti-inflammatory agents, analgesics, anti-histamines, anti-infective agents (e.g., anti-viral, anti-fungal agents, anti-mycotic agents, anti-bacterial agents, components such as dibasic sodium phosphate hepta-hydrate and the like), anti-psoriasis agents, antibiotic agents, wound healing agents, anti-wrinkle agents, skin rejuvenating agents, anti-pigmentation agents, anti-proliferative agents, growth factors, cytotoxic agents, chemotherapeutic agents, and the like, and combinations thereof, anti-parasitic agents, specifically anti-ectoparasitic agents (i.e. compounds exhibiting pediculicidal, ovicidal and scabicidal activity).

The topical alcohol-free thermo labile oily foam compositions of the present invention can further comprise at least one corticosteroid. Exemplary non limiting corticosteroids can comprise commercially available or known corticosteroids are alcometasone, clocortolone, dexamethasone, hydrocortisone, hydrocortisone 21-acetate, prednisone, hydrocortisone 17-valerate, hydrocortisone 17-butyrate, betamethasone valerate, triamcinolone acetonide, flucinonide, desonide, fluticasone, flucinolone acetonide, dexamethasone, dexamethasone 21-phosphate, prednisolone, prednisolone 21-phosphate, haloprednone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone, flumethasone pivalate, flunisolide acetate, flucortolone, fluorometholone, fluperolone acetate, fluprednisolone, fluprednisolone valerate, meprednisone, methyl prednisolone, paramethasone acetate, prednisolamate, prednival, triamcinolone, triamcinolone hexacetonide, cortivazol, formocortal, nivazol, methylprednisone, and their pharmaceutically acceptable free base or free acid forms, salts, esters or ethers, and combinations thereof. The corticosteroid is used in a pharmaceutically effective amount when present.

The topical alcohol-free thermo labile oily foam compositions of the present invention can further comprise at least one antifungal agent such as, but not limited to, diols, allylamines (including naftifine and terbinafine), polyene macrolide antibiotics (including amphotericin and nystatin), triazole derivatives (such as fluconazole), fatty acids (such as caprylic and propionic acid), amorolfine, ciclopirox, olamine, benzoic acid, flucytosine, haloprogin, tolnaftate, undecenoic acid, griseofulvin and imidazole compounds, metronodazole, butocoanzole, ketoconazole, and their pharmaceutically acceptable free base or free acid forms, salts, esters or ethers, and combinations thereof. The antifungal agent is used in a pharmaceutically effective amount when present.

According to a specific embodiment of the present invention, the topical alcohol-free thermo labile oily foam compositions of the present invention comprise at least one ectoparasitic active agent, specifically anti-parasitic and/or insecticidal agent. Preferably, the anti-parasitic and insecticidal agent is selected from agents known for the treatment of scabies and or pediculosis such as, synthetic pyrethroids, lindane (a.k.a a gamma-hexachlorocyclohexane, γ-HCH, gammaxene and Gammallin) or malathion (Diethyl 2-[(dimethoxyphosphorothioyl)sulfanyl]butanedioate). Preferably, the synthetic pyrethroid is permethrin. The anti-parasitic and insecticidal agent is used in an effective amount when present.

The topical alcohol-free thermo labile oily foam compositions of the present invention can further comprise at least one anti-psoriasis agent such as, but no limited to, vitamin D analogs, vitamin A analogs such as esters of vitamin A, e.g. vitamin A palmitate, retinoids, retinols, and retinoic acid; corticosteroids and mixtures thereof. Specifically preferred are Vitamin D or vitamin D analogue, such as, but not limited to, seocalcitol; calcipotriol; calcitriol; tacalcitol; maxacalcitol; paricalcitol; falecalcitriol; 1.alpha., 24S-dihydroxy-vitamin D2; and 1(S),3(R)-dihydroxy-20(R)-[((3-(2-hydroxy-2-propyl)-phenyl)-methoxy)-methyl]-9,10-secopregna-5(Z),7(E),10(19)-triene, as well as mixtures thereof, as sole therapeutically active agent or in combination with at least one other therapeutically active agent, such as, but not limited to, a steroid. The anti-psoriasis agent is used in a therapeutically effective amount when present.

The topical alcohol-free thermo labile oily foam compositions of the present invention can further comprise at least one antibiotic agents such as, but no limited to, a beta-lactam antibiotic, an aminoglycoside, an ansa-type antibiotic, an anthraquinone, an azole, metronidazole, an antibiotic glycopeptide, a macrolide, erythromycin, clindamycin, lincomycin, neomycin, polymyxin, bacitracin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide, a naturally occurring antibiotic compound and analogs, derivatives, salts, ions and complexes thereof. Specifically preferred antibiotic agent is mupirocin and analogs, salts and derivatives thereof. The antibiotic is used in a therapeutically effective amount when present.

The topical alcohol-free thermo labile oily foam compositions of the present invention can further comprise at least one immunosuppressive agents, immunomodulating agents or immune response modifiers such as, but no limited to, ciclosporin, tacrolimus, sirolimus, pimecrolimus, imiquimod, resiquimod, antiproliferative drugs and/or cytotoxic drugs, such as azathioprine, cyclophosphamide, methotrexate, chlorambucil, mycophenolate mofetil (MMF), glucocorticoids, such as prednisolone and others, and antibodies, such as muromonab CD3, antithymocyte globin (ATG), Rho (D) immuneglobin, efalizumab and combinations thereof. The immunosuppressive agent is used in a pharmaceutically effective amount when present.

The topical alcohol-free thermo labile oily foam compositions of the present invention are specifically advantageous for lipophilic or hydrous sensitive therapeutically active agents such as, but not limited to, mupirocin, calcipotriene, and tacrolimus.

According to a further aspect of the present invention, exemplary non-limiting active pharmaceutical ingredients of the compositions of the present invention are selected from a group comprising hormones and therapeutically active analogues, salts and derivatives thereof, e.g. testosterone and progesterone.

According to an additional aspect of the present invention, the topical alcohol-free thermo labile oily foam compositions of the present invention can comprise other therapeutically and/or cosmetically acceptable additives, non-limiting examples of said additives are antioxidants, stabilizing agents, chelating agents, preservative agents, emollients, thickeners, solubilizing agents, suspending agents, tonicity agents, penetration enhancing or modifying agents, crystallization inhibiting agents, anti-irritants, and the like, and combinations thereof.

Non-limiting examples of preservative agents that can be used in the topical alcohol-free thermo labile oily foam compositions of the present invention are benzyl alcohol, alkanols, disodium EDTA (ethylenediamine tetraacetate), EDTA salts, EDTA fatty acid conjugates, isothiazolinone, parabens (e.g., methylparaben and propylparaben), glycols, sorbates, diazolindinyl urea, and the like, and combinations thereof.

Non-limiting examples of emollients that can be used in the topical alcohol-free thermo labile oily foam compositions of the present invention are dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof, and the like, and combinations thereof.

Non-limiting examples of thickening agents that can be used in the topical alcohol-free thermo labile oily foam compositions of the present invention are non-ionic polymers such as, e.g., hydroxyethylcellulose (commercially available under the Trademark Natrosol® 250 or 350), cationic polymers such as Polyquat 37 (commercially available under the Trademark Synthalen® CN), fatty alcohols, fatty acids and alkali salts thereof, and the like, and combinations thereof. It will be appreciated that some thickening agents also can be used as gelling agents.

Non-limiting examples of solubilizing agents that can be used in the topical alcohol-free thermo labile oily foam compositions of the present invention are ethylenediaminetetraacetate, sodium meta-phosphate, succinic acid, cyclodextrin, polyvinylpyrrolidone, diethylammonium-ortho-benzoate, or micell-forming solubilizers such as tweens and spans (e.g., Tween 80), and the like, and combinations thereof. Other suitable solubilizers can comprise, e.g., polyoxyethylene sorbitan fatty acid ester, polyoxyethylene n-alkyl ethers, n-alkyl amine n-oxides, poloxamers, organic solvents, phospholipids, cyclodextrins, and the like, and combinations thereof.

Non-limiting examples of penetration enhancing or penetration modifying agents that can be used in the topical alcohol-free thermo labile oily foam compositions of the present invention are dimethylsulfoxide (DMSO), dimethyl formamide (DMF), allantoin, urazole, N-dimethylacetamide (DMA), decylmethylsulfoxide (C10MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), glycerin, hyaluronic acid, transcutol, and the like, and combinations thereof. Certain oil components (e.g., certain vegetable oils such as safflower oil, cottonseed oil and corn oil) also can exhibit penetration enhancing or penetration modifying properties.

The present invention provides a method for treating, alleviating or preventing a disease and/or condition, which method comprises topically applying to the patient's skin an effective amount of a topical alcohol-free thermo labile oily foam composition of the present invention. Said topical application can be employed for local and/or systemic delivery of at least one therapeutically active pharmaceutical ingredient or ectoparasitic active ingredient. Said disease or condition can comprise, but are not limited to, intractable lichenified or hyperkeratotic lesions, autoimmune diseases, fungal infections, viral infections, bacterial infections, ectoparasitosis, primary and secondary skin infections, inflammations of the skin, dermatoses, cut, burns, insect bites, tinea pedis hair growth, hair removal, hormonal deficiencies. More specifically, said disease or condition can comprise, but are not limited to, psoriasis, scabies, pediculosis, atopic dermatitis, diaper rash, ichtiosis, allergic pruritus, and other skin conditions such as seborrheic dermatitis, scalp dandruff, tinea vesicular, purities, burns, cuts, wounds, lesions, ulcers, impetigo, genital or anus warts, aphtha, otitis externa, otitis media, hypogonadism, pain, infected dermatoses e.g., infected eczema, infected traumatic lesions e.g., abrasions, insect bites, local antibiotic therapy pre and post operative, oral mucositis, oral candidadiatis, herpes, otomycosis, Candida, tinea cruris (Jock Itch), skin related allergy symptoms, folliculitis, furunculosis, paronychia, lichen simplex chronicus, hypertrophic lichen planus, palmar plantar keratodermas (PPK) and ecthyma, basal cell carcinoma, and actinic keratoses.

The topical alcohol-free thermo labile oily foam compositions of the present invention can be used as prophylaxis of bacterial contamination of small cuts and wounds, abrasions, incisions and other lesions.

After application to the treatment area, the foam structure of the topical alcohol-free thermo labile oily foam compositions of the present invention readily collapse without rubbing or application of sheer force. The readily collapsing composition is advantageous when applying said compositions to painful or infection-sensitive areas (such as cuts, incisions, burns, dermatitis (e.g. diaper-rash), inflammation, lesions, etc.). A further advantage of the topical alcohol-free thermo labile oily foam compositions of the present invention is where they are used on difficult to apply body areas (such as vagina, ear canal, eyes, nasal cavity, etc.). A further advantage is the use of the invention compositions by disabled patients. An additional benefit is the maintenance of sterility of the treatment site, the applied composition, the canister, and the composition remainder in the canister. The application of the topical alcohol-free thermo labile oily foam compositions of the present invention, which does not require rubbing or touching the application site, obviates contamination of the treatment, site, which is especially important when applied to infection-sensitive areas (such as cuts, incisions, burns, dermatitis (e.g. diaper-rash), inflammation, lesions etc.).

Another advantage of application of the topical alcohol-free thermo labile oily foam compositions of the present invention while obviating the need for touching the application site (i.e. rubbing or applying shear force), is the avoidance of transfer of the composition components, specifically the pharmaceutical active ingredient or ectoparasitic active ingredient, to other body parts or other individuals, as the hands of the applying individual stay clean.

The present invention provides a method of producing a topical alcohol-free thermo labile oily foam compositions, which comprises mixing all of the ingredients excluding the propellant, heating the mixture to a temperature of from about 40° C. to about 100° C., homogenizing the mixture, optionally cooling the mixture to a temperature above about 40° C., pouring the resulting mixture into an aluminum aerosol spraying canister, attaching a valve to the canister, supplying vacuum to the canister and sealing the canister. A hydrocarbon propellant mixture is then added and an actuator is assembled on the valve.

The present invention additionally provides a method of manufacture of said topical alcohol-free thermo labile oily foam compositions comprising providing the therapeutically active agent or ectoparasitic active ingredient in a first vessel, mixing the carrier system components in a second vessel to obtain a carrier mixture, heating the carrier mixture to a temperature of from about 40° C. to about 100° C., adjusting the carrier mixture to a temperature suitable for mixing with the second vessel, and adding the contents of the first vessel to the second vessel to obtain an oily composition, optionally homogenizing the composition, pouring the obtained composition into an pressurized aerosol spraying canister, attaching a valve to the canister, applying vacuum at a pressure of from about −0.1 bar to about −0.7 bar to the canister and subsequently sealing the canister. Following said sealing, adding a hydrocarbon propellant mixture and attaching an actuator onto canister valve.

The therapeutically active agent or ectoparasitic active ingredient provided in the first vessel is optionally processed prior to its addition to the second vessel. Said processing may vary and depends on the characteristics of either the therapeutically active agent or ectoparasitic active ingredient and the components of carrier system to which it is added. The processing usually comprises a solution or a suspension containing the therapeutically active agent or ectoparasitic active ingredient obtainable by using techniques well-known in the art.

Said optional homogenization, can be prior to the addition of the therapeutically effective pharmaceutical ingredient or ectoparasitic active ingredient into the carrier system mixture or after it.

A suitable temperature for mixing the contents of the first and second vessels is from about 15° C. to about 50° C.

The topical alcohol-free thermo labile oily foam compositions obtained by the process described herein can be stored for up to about 30 days. Storage is preferably done in a temperature of from about 15° C. to about 30° C.

In a further aspect of the invention, there is provided a topical alcohol-free thermo labile oily foam composition comprising (i) at least one active pharmaceutical ingredient or ectoparasitic active ingredient; (ii) at least 20% w/w of at least one lipophilic component; (iii) at least 10% w/w of at least one non-ionic surfactant; (iv) at least 0.5% of at least one fatty alcohol or fatty acid or ester thereof with melting point above 30° C., and; (v) at least 7% of propellant selected from propane, butane, isobutane and combinations thereof. Said composition may additionally comprise at least 15% w/w of a hydrophilic component and may also comprise up to 5% hydrogenated oil.

In a preferred embodiment of the invention, there is provided a topical alcohol-free thermo labile oily foam composition comprising (i) at least one active pharmaceutical ingredient or ectoparasitic active ingredient selected from mupirocin, calcitriol, calcipotriene, betamethasone, mometasone, fluticasone, hydrocortisone, imiquimod, tacrolimus, pimecrolimus, permethrin, lindane and malathion and their therapeutically active analogs, salts and derivatives; (ii) at least about 20% w/w and more particularly about 40 to about 95% w/w of at least one lipophilic component selected from castor oil, oleyl alcohol, caprylic/capric triglyceride, and combinations thereof; (iii) at least about 10% w/w of at least one non-ionic surfactant selected from polysorbate 20, polysorbate 80 and methyl glucose sesquistearate; (iv) at least about 0.5% of at least one fatty alcohol or fatty acid or ester thereof with melting point above 30° C., selected from cetyl alcohol and stearyl alcohol; (v) at least about 7% of propellant selected from propane, butane, isobutane and combinations thereof. Said composition may additionally comprise at least about 5 to about 70% w/w and more particularly at least about 15% w/w of a hydrophilic component selected from hexylene glycol, MPEG 350, dimethyl isosorbide, and combinations thereof and may also additionally comprise up to 5% hydrogenated oil, preferably hydrogenated castor oil or tri-hydroxy stearyl.

In one embodiment of the present invention, there is provided a topical alcohol-free thermo labile oily foam composition comprising about 1% to about 3% w/w and more particularly about 2.0% w/w mupirocin, about 12.0% w/w to about 16.0% w/w castor oil, about 8.0% w/w to about 12.0% w/w oleyl alcohol, about 24.0% w/w to about 28.0% w/w % w/w caprylic/capric triglyceride, about 18.0% w/w to about 22.0% w/w MPEG 350, about 13.0% w/w to about 17.0% w/w polysorbate 20, about 5.0% w/w to about 9.0% w/w cetyl alcohol, about 0.5% w/w to about 4.0% w/w stearyl alcohol, about 0.5% w/w to about 4.0% w/w hydrogenated castor oil, and about 8.0 to about 12.0% w/w of propellant which is a mixture of propane, butane and isobutane.

In another preferred embodiment of the present invention is a topical alcohol-free thermo labile oily foam composition comprising about 1% to about 3% w/w and more particularly about 2.0% w/w mupirocin, about 12.0% w/w to about 16.0% w/w castor oil, about 8.0% w/w to about 12% w/w oleyl alcohol, about 18.0% w/w to about 22.0% MPEG 350, about 6.0% w/w to about 11.0% w/w dimethyl isosorbide, about 10.0% w/w to about 14.0% w/w hexylene glycol, about 13.0% w/w to about 17.0% w/w polysorbate 20, about 10.0% w/w to about 14.0% w/w cetyl alcohol, about 1.0% w/w to about 5% w/w stearyl alcohol, about 0.5% w/w to about 4.0% w/w hydrogenated castor oil, and about 8.0 to about 12.0% w/w of propellant which is a mixture of propane, butane and isobutane.

In yet another embodiment of the present invention, there is provided a topical alcohol-free thermo labile oily foam composition comprising about 0.001% to about 0.01% w/w and more particularly about 0.005% w/w calcipotriene, about 12.0% to about 16.0% w/w castor oil, about 8.0% w/w to about 12.0% w/w oleyl alcohol, about 24.0% to about 28.0% w/w caprylic/capric triglyceride, about 18.0% to about 22.0% w/w MPEG 350, about 13.0% to about 17.0% w/w polysorbate 20, about 7.0% w/w to about 11.0% w/w cetyl alcohol, about 2.0% to about 6.5% w/w stearyl alcohol, about 0.5% to about 4.0% w/w hydrogenated castor oil, and about 7.0% w/w to about 20.0% w/w of propellant which is a mixture of propane, butane and isobutane.

In an additional embodiment of the present invention there is provided a topical alcohol-free thermo labile oily foam composition comprising about 0.001% to about 0.01% w/w and more particularly about 0.005% w/w calcipotriene, about 0.01% to about 0.1% w/w and more particularly about 0.064% w/w betamethasone dipropionate, about 12.0% w/w to about 16.0% w/w castor oil, about 8.0% w/w to about 12.0% w/w oleyl alcohol, about 24.0% w/w to about 28.0% w/w caprylic/capric triglyceride, about 18.0% w/w to about 22.0% w/w MPEG 350, about 13.0% w/w to about 17.% w/w polysorbate 20, about 7.0% w/w to about 11.0% w/w cetyl alcohol, about 2.0% w/w to about 6.5% w/w stearyl alcohol, about 0.5% w/w to about 4.0% w/w hydrogenated castor oil, and about 7.0% w/w to about 20.0% w/w of propellant which is a mixture of propane, butane and isobutane.

In a yet additional embodiment of the present invention there are provided topical alcohol-free thermo labile oily foam compositions comprising about 0.01 to about 0.05% w/w and more particularly about 0.1% w/w mometasone furoate, about 12.0% w/w to about 16.0% w/w castor oil, about 8.0% w/w to about 12.0% w/w oleyl alcohol, about 18.0% w/w to about 22.0% w/w MPEG 350, about 6.0% w/w to about 11.0% w/w dimethyl isosorbide, about 10.0% w/w to about 14.0% w/w hexylene glycol, about 13.0% w/w to about 17.% w/w polysorbate 20, about 11.0% w/w to about 15.0% w/w cetyl alcohol, about 2.0% w/w to about 6.0% w/w stearyl alcohol, about 0.5% w/w to about 4.0% w/w hydrogenated castor oil, and about 8.0% to about 12.0% w/w of propellant which is a mixture of propane, butane and isobutane.

EXAMPLES

Reference is now made to the following examples, which together with the above description illustrate the invention in a non-limiting fashion. Generally, the nomenclature used herein and the laboratory procedures utilized in the present invention comprise chemical and analytical techniques with which on skilled in the art is familiar. Unless otherwise defined, technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Examples 1-5—Topical Alcohol-Free Thermo Labile Oily Foamable Mupirocin Compositions

TABLE 1

| Ingredient | Example 1 % w/w | Example 2 % w/w | Example 3 % w/w | Example 4 % w/w | Example 5 % w/w |
|---|---|---|---|---|---|
| Mupirocin | 2.0 | 2.0 | 2.0 | 2.0 | 2.0 |
| Castor Oil | 14.9 | 14.9 | 14.9 | 14.9 | 14.9 |
| Oleyl Alcohol | 10.0 | 10.0 | 0.0 | 10.0 | 10.0 |
| Polysorbate 20 | 15.0 | 15.0 | 15.0 | 15.0 | 15.0 |
| MPEG 350 | 20.0 | 20.0 | 20.0 | 20.0 | 20.0 |
| Cetyl Alcohol | 7.0 | 12.0 | 12.0 | 14.0 | 7.0 |
| Stearyl Alcohol | 2.0 | 3.0 | 3.0 | 3.5 | 2.0 |
| Caprylic/Capric Triglyceride | 26.1 | 0.0 | 6.1 | 0.0 | 27.9 |
| Dimethyl Isosorbide | 0.0 | 8.90 | 15.0 | 8.6 | 0.0 |
| Hexylene Glycol | 0.0 | 12.0 | 12.0 | 12.0 | 0.0 |
| Hydrogenated Castor Oil | 2.0 | 2.0 | 0.0 | 0.0 | 0.8 |
| Methyl-Glucose Sesquistearate (Glucate ™) | 0.0 | 0.2 | 0.0 | 0.0 | 0.4 |
| Total | 100.0 | 100.0 | 100.0 | 100.0 | 100.0 |
| Propellant* | 8.012-.0 | 8.012-.0 | 8.012-.0 | 8.012-.0 | 8.012-.0 |

* Propellant is added to the total weight of the composition; hence the percentage of total composition, plus propellant can exceed 100% w/w The carrier system components were combined in a vessel and heated to obtain a mixture, the mixture was cooled to about 40° C. and Mupirocin was added to obtain an oily composition. The obtained composition was poured into a pressurized aerosol spraying canister, a valve was attached to the canister, vacuum was applied to the canister at a pressure of about −0.5 bar and the valve was thereafter crimped to seal the canister. The hydrocarbon propellant mixture was then added and an actuator was assembled on the valve.

Examples 6 and 7 below were prepared according to the procedure described for examples 1-5 and in the specifications.

Example 6—Topical Alcohol-Free Thermo Labile Calcipotriene Oily Foam Composition

TABLE 2

| Ingredient | % w/w |
|---|---|
| Calcipotriene | 0.005 |
| Castor Oil | 14.9 |
| Oleyl Alcohol | 10.0 |
| Polysorbate 20 | 15.0 |
| MPEG 350 | 20.0 |
| Cetyl Alcohol | 9.0 |
| Stearyl Alcohol | 4.5 |
| Caprylic/Capric Triglyceride | 25.595 |
| Hydrogenated Castor Oil | 1.0 |
| Total | 100.0 |
| Propellant* | 7.0-20.0 |

*Propellant is added to the total weight of the composition, hence the percentage of total composition, plus propellant can exceed 100% w/w Example 7—Topical Alcohol-Free Thermo Labile Calcipotriene and Betamethasone Dipropionate Oily Foam Composition

TABLE 3

| Ingredient | % w/w |
|---|---|
| Calcipotriene | 0.005 |
| Betamethasone dipropionate | 0.064 |
| Castor Oil | 14.9 |
| Oleyl Alcohol | 10.0 |
| Polysorbate 20 | 15.0 |
| MPEG 350 | 20.0 |
| Cetyl Alcohol | 9.0 |
| Stearyl Alcohol | 4.5 |
| Caprylic/Capric Triglyceride | 25.531 |
| Hydrogenated Castor Oil | 1.0 |
| Total | 100.0 |
| Propellant* | 7.0-20.0 |

*Propellant is added to the total weight of the composition; hence the percentage of total composition, plus propellant can exceed 100% w/w.

What is claimed is:

1. A method of treating, alleviating or at least one of (i) a dermatological or mucosal disease or disorder and, (ii) ectoparasitosis, comprising topically administering to a subject in need thereof an effective amount of a topical alcohol-free thermo labile oily foam composition, the composition comprising
    (i) at least one active pharmaceutical ingredient or ectoparasitic active ingredient;
    (ii) at least about 20% w/w of at least one lipophilic component;
    (iii) at least about 10% w/w of at least one non-ionic surfactant;
    (iv) at least about 0.5% w/w of at least one fatty alcohol or fatty acid or ester thereof with melting point above 30° C., and;
    (v) at least about 7% w/w of propellant selected from propane, butane, isobutane and combinations thereof; said composition optionally comprising at least about 5% to about 70% w/w of a hydrophilic component, optionally comprising up to about 5% w/w hydrogenated oil and optionally comprising a penetration enhancer; and wherein the composition is a readily collapsible foam composition.

2. The method of claim 1 wherein the subject is affected with a dermatological or mucosal disease or disorder or ectoparasitosis is selected from autoimmune diseases, fungal infections, viral infections, bacterial infections, primary and secondary skin infections, inflammations of the skin, dermatoses, cut, burns, impetigo, insects bites and/or ectoparasitosis by ticks, lice, fleas or mites.

3. A method of treating, alleviating or at least one of (i) a dermatological or mucosal disease or disorder and, (ii) ectoparasitosis, comprising topically administering to a subject in need thereof a therapeutically effective amount of the topical alcohol-free thermo labile oily foam composition comprising:
    (i) at least one active pharmaceutical ingredient or ectoparasitic active ingredient;
    (ii) at least about 20% w/w of at least one lipophilic component;
    (iii) at least about 10% w/w of at least one non-ionic surfactant;
    (iv) at least about 0.5% w/w of at least one fatty alcohol or fatty acid or ester thereof with melting point above 30° C., and;

(v) at least about 7% w/w of propellant selected from propane, butane, isobutane and combinations thereof; said composition optionally comprising about 5 to about 70% w/w of a hydrophilic component and optionally comprising up to about 5% w/w hydrogenated oil; and wherein the composition is a readily collapsible foam composition.

4. The method of claim 3 wherein the subject is affected with a dermatological or mucosal disease or disorder or ectoparasitosis is selected from autoimmune diseases, fungal infections, viral infections, bacterial infections, primary and secondary skin infections, inflammations of the skin, dermatoses, cut, burns, impetigo, insects bites and ectoparasitosis by ticks, lice, fleas or mites.

5. The method of claim 3 wherein the topical alcohol-free thermo labile oily foam composition contains at least one active pharmaceutical ingredient or ectoparasitic active ingredient that is lipophilic or hydrous sensitive.

6. The method of claim 3 wherein the active pharmaceutical ingredient is one or more agent selected from mupirocin, calcipotriene, calcitriol, betamethasone, clobetasol, mometasone, tacrolimus, pimecrolimus, and their therapeutically active analogs, salts and derivatives thereof.

7. The method of claim 3 wherein the ectoparasitic active ingredient is one or more agent selected from permethrin, lindane, malathion and their analogs, salts or derivatives, and mixtures thereof.

8. The method according to claim 3 wherein said hydrogenated oil is hydrogenated castor oil.

9. A method for topically delivering a therapeutically effective amount of an active pharmaceutical ingredient or ectoparasitic active ingredient by topically applying a therapeutically effective amount of a topical alcohol-free thermo labile oily foam composition to a subject in need thereof, the composition comprising
(i) at least one active pharmaceutical ingredient or ectoparasitic active ingredient;
(ii) at least about 20% w/w of at least one lipophilic component;
(iii) at least about 10% w/w of at least one non-ionic surfactant;
(iv) at least about 0.5% w/w of at least one fatty alcohol or fatty acid or ester thereof with melting point above 30° C., and;
(v) at least about 7% w/w of propellant selected from propane, butane, isobutane and combinations thereof;
said composition optionally comprising at least about 5% to about 70% w/w of a hydrophilic component, optionally comprising up to about 5% w/w hydrogenated oil and optionally comprising a penetration enhancer; and wherein the composition is a readily collapsible foam composition.

10. A method according to claim 9 wherein said topical delivery is for topical and/or systemic treatment, alleviation of a disease, condition and/or disorder, and ectoparasitosis selected from autoimmune diseases, fungal infections, viral infections, bacterial infections, primary and secondary skin infections, inflammations of the skin, dermatoses, cuts, burns, impetigo, insect bites and/or ectoparasitosis by ticks, lice, fleas or mites.

11. A method of treating, alleviating or at least one of (i) a dermatological or mucosal disease or disorder comprising topically administering to a subject in need thereof a therapeutically effective amount of the topical alcohol-free thermo labile oily foam composition comprising:
(i) at least one active pharmaceutical ingredient;
(ii) at least about 20% w/w of at least one lipophilic component;
(iii) at least about 10% w/w of at least one non-ionic surfactant;
(iv) at least about 0.5% w/w of at least one fatty alcohol or fatty acid or ester thereof with melting point above 30° C., and;
(v) at least about 7% w/w of propellant selected from propane, butane, isobutane and combinations thereof;
said composition optionally comprising about 5 to about 70% w/w of a hydrophilic component and optionally comprising up to about 5% w/w hydrogenated oil; and wherein the composition is a readily collapsible foam composition.

12. The method of claim 11 wherein the subject is affected with a dermatological or mucosal disease or disorder selected from autoimmune diseases, fungal infections, viral infections, bacterial infections, primary and secondary skin infections, inflammations of the skin, dermatoses, cut, burns or impetigo.

13. The method of claim 11 wherein the topical alcohol-free thermo labile oily foam composition contains at least one active pharmaceutical ingredient that is lipophilic or hydrous sensitive.

14. The method of claim 11 wherein the active pharmaceutical ingredient is one or more agent selected from mupirocin, calcipotriene, calcitriol, betamethasone, clobetasol, mometasone, tacrolimus, pimecrolimus, and their therapeutically active analogs, salts and derivatives thereof.

* * * * *